United States Patent [19]

Wagner

[11] Patent Number: 4,828,982

[45] Date of Patent: May 9, 1989

[54] VESTICLES AND USE THEREOF IN AN ENZYME ASSAY

[75] Inventor: Daniel B. Wagner, Raleigh, N.C.

[73] Assignee: Becton, Dickinson & Company, Franklin Lakes, N.J.

[21] Appl. No.: 737,777

[22] Filed: May 28, 1985

[51] Int. Cl.[4] .......................................... G01N 33/543
[52] U.S. Cl. .......................................... 435/7; 435/18;
435/19; 435/21; 435/810; 436/501; 436/518;
436/536; 436/808; 436/829
[58] Field of Search ................. 435/7, 18, 19, 21, 810;
436/501, 518, 528, 829, 536, 808

[56] References Cited

U.S. PATENT DOCUMENTS

| 4,193,983 | 3/1980 | Ullman et al. | 435/7 |
| 4,235,871 | 11/1980 | Papahadjopoulos et al. | 424/92 |
| 4,463,090 | 7/1984 | Harris | 436/829 |
| 4,603,044 | 7/1986 | Geho et al. | 436/829 |
| 4,666,830 | 5/1987 | Wagner | 436/829 |
| 4,695,554 | 9/1987 | O'Connell et al. | 436/536 |

OTHER PUBLICATIONS

Mahler et al., *Biological Chemistry*, Harper & Row Publishers, Inc., New York, 1966, pp. 511-513.
McDougall et al., *Proc. Nat. Acad. Sci.* (U.S.A.), 71, 3487-3491, 1974.
Engvall et al., in Feldmann et al., Ed., *First International Symposium on Immunoenzymatic Techniques*, North-Holland Publishing Company, Amsterdam, 1976, pp. 135-147.
R. Neumann et al., *Chem. Abs.* 104, 110158f, 1986.

*Primary Examiner*—Robert J. Warden
*Assistant Examiner*—Daisy A. Saunders
*Attorney, Agent, or Firm*—Elliot M. Olstein

[57] ABSTRACT

A sac is produced by use of a compound which includes a hydrophobic portion and a polar group which is hydrolyzable by an enzyme and which is spaced from the hydrophobic portion by a hydrophilic portion which does not have a polarity sufficient to form a vesicle. A detectable marker may be released from the sac by use of a hydrolase enzyme, whereby the sac may be used as a substrate in an enzyme assay.

34 Claims, No Drawings

VESICLES AND USE THEREOF IN AN ENZYME ASSAY

This invention relates to vesicles and sacs and to the use thereof. This invention further relates to an assay for a ligand which employs a vesicle or sac as a component thereof.

Vesicles or sacs are generally produced from amphiphilic compounds (compounds having both a hydrophobic portion and a hydrophilic portion), with such vesicles or sacs being most commonly produced from lipids; in particular phospholipids. When the vesicles or sacs are produced from lipids they are most often referred to as liposomes.

As known in the art, such vesicles or sacs may be formed in a manner such as to encapsulate a material in the interior of the sac. Thus, for example, such sacs have been used to encapsulate biologically active materials; for example, a therapeutic drug.

In addition, such sacs have been employed to encapsulate a detectable marker for use in an assay for a ligand. Thus, for example, in an assay for a ligand, the tracer used in the assay may be produced by coupling the ligand or appropriate analog thereof to a sac containing a detectable marker. In such an assay, for example, the tracer and ligand to be determined (analyte) may compete for a limited number of bindings sites on a binder for both the tracer and analyte. The amount of tracer which is bound to the binder is inversely proportional to the amount of analyte in the sample. The bound and/or unbound portion of the tracer is determined as a measure of analyte by releasing the marker from the sac.

In such assays, in producing a tracer, it is necessary to conjugate a ligand to the sac containing the detectable marker. It has been found that in many cases such tracers do not have the requisite stability; i.e., after a period of time, the sac deteriorates and/or the ligand does not remain coupled to the sac. In addition, it is necessary to produce and store sacs conjugated to a variety of ligands for use in assays for a variety of analytes.

In accordance with one aspect of the present invention, there is provided an improved sac or vesicle wherein at least a portion of the sac is formed from a compound having the following structural formula I:

X—Y—Z         (I)

Wherein
X is a hydrophobic radical;
Y is a hydrophilic radical having a polarity which is insufficient to form a vesicle; and
Z is a polar group which is hydrolyzable by an enzyme, in particular a hydrolase enzyme.

Applicant has found that by utilizing a compound of the type hereinabove described in forming the wall of a sac, it is possible to lyse the sac by use of an appropriate enzyme so as to release the contents thereof. Although applicant does not intend that the present invention be limited by any theoretical reasoning, it is believed that by spacing the hydrolyzable polar group from the hydrophobic portion of the compound by use of a hydrophilic spacer group, the polar group can be hydrolyzed by a hydrolase enzyme. Since the hydrophilic spacer group, in the absence of the polar group, does not have a sufficient polarity to maintain the sac or vesicle intact, upon hydrolysis of the polar group, the sac is ruptured to release the contents thereof.

It is believed that the close proximity of a polar group to a hydrophobic radical prevents hydrolysis by a hydrolase enzyme, and in accordance with the present invention, the polar head group is spaced from the hydrophobic group by a hydrophilic group which permits hydrolysis. The hydrophobic group may be one which is commonly used in vesicles. In contrast, if the hydrophilic spacer group is omitted, the polar group is not hydrolyzed by a hydrolase enzyme, and the sac is not ruptured.

The hydrophobic radical represented by X may be any one of a wide variety of hydrophobic radicals which are known to be suitable as the hydrophobic portion of a compound used in producing a sac. As representative examples of suitable hydrophobic radicals, there may be mentioned hydrophobic radicals represented by the following structural formula II and III:

or

wherein each of $R_1$, and $R_2$ is a substituted or unsubstituted hydrocarbon radical (saturated or unsaturated) having at least 11 carbon atoms and may be the same or different radicals and $R_1$ and $R_2$ may be linked together to form a cyclic compound, each of $B_1$ and $B_2$ is —$CH_2$—, —C(O)NH—, —NH—, —C(O)O— —O—, —S—, and may be the same or different radicals;

T is —NH— or a substituted $C_1$ to $C_3$ hydrocarbon wherein the substituent group is —S—; —NH—, or —C(O)—; and A is a hydrocarbon radical having from 1 to 4 carbon atoms, preferably 3 or 4 carbon atoms.

The hydrophilic radical represented by Y in the hereinabove described structural formula does not have a polarity sufficient to form a sac and/or prevent the sac from rupturing in the absence of the polar group Z. The hydrophilic radical is preferably a peptide formed from at least two amino acids and the molecular weight is such that the peptide is hydrophilic (if the molecular weight is too high the peptide may become hydrophobic). The amino acids forming the peptide generally do not have more than four carbon atoms; for example, B-alanine, glycine, serine, threonine, etc.

As representative examples of polar groups which are hydrolyzable by an enzyme, and which in combination with the hydrophilic spacer radical Y are sufficient to produce a sac, there may be mentioned, phosphate and sulfate esters. The polar group may be directly substituted on the terminal amino acid of the peptide or may be connected through a peptide linkage to a hydrocarbon spacer group, which includes the polar head group, with the spacer group being insufficient to change to hydrophilic nature of the peptide.

A preferred class of wall forming compounds is represented by the following structural formulas, with the compounds generally being formed by coupling a long chain amine to a short chain peptide, which is provided with a phosphate group with the compounds represented by following formulas IV & VI, being particularly preferred.

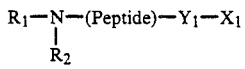

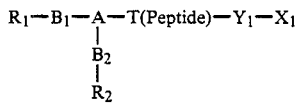

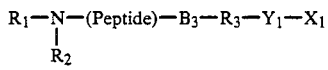

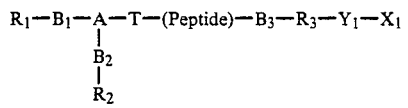

Wherein $R_1$, $R_2$, $B_1$, $B_2$, A, and T are as hereinabove described; $B_3$ is —C(O)—, or —NH— and forms a peptide linkage with the terminal amino acid of the peptide; $R_3$ is a hydrocarbon radical having no more than 10 carbons atoms, $X_1$ is hydrogen or a cation, such as sodium; for example $B_3$ may be —C(O)— and $R_3$ may be phenalkyl.

$Y_1$ is —$SO_4$— or —$PO_4$—; and the peptide is a hydrophilic peptide formed from amino acids having no more than four carbon atoms, with the peptide generally being formed from no more than ten amino acids.

The peptide employed in producing the compounds used for forming a sac may be synthesized by any one of a variety of procedures of producing a peptide from amino acids. The hydrophobic radical may be linked to the peptide, by standard techniques for peptide synthesis. The precursor comprised of the hydrophobic radical coupled to a peptide may then be treated to provide the peptide portion with a terminal polar group which can be cleaved (hydrolyzed) by an enzyme. For example, if the terminal amino acid of the peptide includes a hydroxyl groups, such terminal amino acid may be phosphorylated or sulfonated by standard techniques. Alternatively, the terminal amino acid may be functionalized to provide a hydroxyl group for phosphorylation or sulfonation.

The sacs produced in accordance with the present invention may be comprised entirely of one or more compounds of the type hereinabove described, or the sac or vesicle may be comprised of one or more compounds of the type hereinabove described and one or more other compounds suitable for producing sacs. As representative examples of compounds which can be used in addition to those having a hydrolyzable polar group of the type hereinabove described, there may be mentioned: lipids, including phospholipids, glycolipids, steroids, relatively long chain alkyl esters; e.g., alkyl phosphates, fatty acid esters, e.g. lecithin, fatty amines and the like. A mixture of fatty materials may be employed such as a combination of neutral steroid, a charged amphiphile and a phospolipid. As illustrative examples of phospholipids there may be mentioned sphingomyelin, dipalmitoyl, lecithin, and the like. As representative steroids, there may be mentioned cholesterol, cholestanol, lanosterol, and the like. As representative examples of charged amphiphilic compounds, which generally contain from 12 to 30 carbon atoms, there may be mentioned mono- or dialkyl phosphate ester, quaternary ammonium salts, or an alkylamine; e.g., dicetyl phosphate, stearyl amine, hexadecyl amine, dilauryl phosphate, dioctadecyl sulfonate, didodecyl dioctylammonium formide, and the like.

The sacs or vesicles, which have at least a portion of the wall thereof formed from a compound having the hereinabove described structural formula may be produced by procedures generally available in the art for producing sacs or vesicles. For example, the sac or vesicle may be produced by a reverse phase evaporation technique wherein the compound or compounds used in producing the sac or vesicle are initially dissolved in an organic phase, followed by addition of an aqueous phase and forming of a homogeneous emulsion. After forming the emulsion, the organic solvent is evaporated to form a gel-like material, and such gel may be converted to a sac or vesicle by agitation or dispersion in an aqueous media such as a buffer solution.

Procedures for producing vesicles or sacs are generally known in the art, and such procedures may be employed for producing a sac or vesicle in accordance with the present invention.

Details with respect to the preparation of sacs are set forth in U.S. Pat. No. 4,241,046; U.S. Pat. No. 4,342,826, and P.C.T. International Publication No. Patent WO 80-01515.

As known in the art, if a material is to be encapsulated in the sac, such material may be encapsulated by including the material in an aqueous solution in which the sac or vesicle is formed. Alternatively, the material may be encapsulated into a previously formed "empty" sac by the procedure described in U.S. application Ser. No. 650,200, filed on Sept. 13, 1984.

In accordance with another aspect of the present invention, a sac of the type hereinabove described, including a detectable marker, may be used as a substrate in an assay employing a tracer in which an enzyme is used as the label, often referred to as an enzyme assay or an enzyme between the enzyme portion of the tracer and the sac hydrolyzes the polar group of the sac, whereby the sac is ruptured and the marker included in the sac is released. The amount and/or rate of release of the marker may be determined as a measure of analyte in the sample.

In an enzyme assay, the tracer which is employed in the assay is a ligand having an enzyme coupled thereto. The ligand which is employed in producing the tracer is dependent upon the assay which is employed. Thus, for example, if the assay is for an analyte which is an antigen or a hapten, the ligand portion of the tracer may be the analyte or appropriate analog thereof. As used herein, the term "appropriate analog", when referring to an analog of the analyte, means that the analog of the analyte is bound by the binder for the analyte which is used in the assay.

The ligand portion of the tracer may also be an antibody to the analyte. Similarly, if the analyte is an antibody, the ligand portion of the tracer may be an antigen bound by the antibody or an antibody elicited in response to the analyte.

In any event, the ligand portion of the tracer is bound by one of the binder or the analyte. Thus, for example, in a so called "sandwich" assay, the analyte may be bound by the binder and the tracer bound by the analyte, whereby the amount of tracer bound to the binder through the analyte is dependent upon the amount of analyte in the sample. In an alternative procedure, the binder may be a binder for both the analyte and the ligand portion of the tracer, whereby the amount of tracer bound to the binder is inversely proportional to the amount of analyte in the sample.

In accordance with the procedure of the present invention, the sac including the detectable marker is employed as a substrate for the enzyme so as to determine the bound and/or free portion of the tracer as a measure of analyte in the sample. By contacting the bound and/or free tracer with a sac of the type hereinabove described including a detectable marker, the marker is released from the sac whereby determination of the amount and/or rate of the released marker can be employed as a measure of analyte in the sample.

The marker which is included within the sac for use in an assay may be any one of a wide variety of detectable markers, including but not limited to radioisotopes, chromogens (an absorbing dye and/or a fluorescent material), a luminescent compound, spin labels, etc. Such detectable markers, and the methods for determining the markers are generally known in the art, and no further details in this respect are deemed necessary for a complete understanding of the invention. The preferred types of markers are dyes with a high extinction coefficient, such as sulforhodmine B, fluorescent dye such as carboxyfluorescein, and the like.

The assay may be a solid phase assay of a type known in the art wherein the binder is supported on a solid support. As generally known in the art, the use of a solid phase facilitates separation of bound and free portions of the tracer.

As a representative example of an assay procedure in accordance with the present invention, there may be mentioned an assay wherein a sample containing or suspected of containing the analyte is incubated with a tracer, which is the analyte or appropriate analog thereof coupled to an appropriate enzyme, and a binder specific for both the analyte and tracer. The incubation results in competition between the tracer and analyte for binding sites on the binder, with the amount of tracer which is bound to the binder being inversely proportional to the amount of analyte in the sample.

The bound and free components are separated from each other, and the free portion is then contacted with sacs of the type hereinabove described, which include a detectable marker therein, under conditions which prevent premature rupturing of the sacs (the sacs are only ruptured by contact with the enzyme portion of the tracer). This portion of the assay is generally run in an appropriately buffered aqueous medium which is isotonic with the osmolarity of the sacs. Thus, conditions of temperature, pH and ionic concentrations are controlled to prevent premature rupturing of the sacs. Thus, for example, an aqueous buffered medium is provided which is isotonic with the osmolarity of the sacs, and in general, such a buffer provides a pH in the order of from 5-9.

As a result of the contact between the enzyme portion of the tracer and the sacs, the polar group of the sacs is hydrolyzed, and the sacs are ruptured to release marker. The rate at which the marker is released into the medium and/or the amount of marker which is released into the medium is dependent upon the concentration of tracer present, with an increasing amount of tracer resulting in an increase in the rate and/or amount of release of marker into the medium. Thus, by determining the rate at which marker is released into the medium, or in the alternative, by determining the amount of marker in the medium after a fixed period of time, and comparing such values with those obtained by an identical procedure using known amounts of analyte (standard analyte having known concentrations), there can be obtained a measurement of the amount of analyte present in the sample.

The rate can be determined either kinetically by measuring the signal intensity increase with time, or by the end point method, where the reaction is allowed to proceed for a fixed length of time and is then stopped (for example, by increasing the pH), and the color (or fluorescent, or luminescence, as the case may be) is measured. The higher the reaction rate, the stronger will be the signal at the end point.

The sample volume which is used in the assay is selected so as to prevent a "runaway" rate for release of the marker; i.e., to provide a detectable rate of change with time and/or a detectable difference in the amount of marker released dependent upon concentration of analyte in the original sample. Thus, as the expected analyte concentration increases, the sample volume may be decreased so as to provide for a detectable change in rate and/or a detectable difference in the amount of analyte in a given sample.

The above procedure is only a representative assay procedure. Other assay techniques of the type generally employed in an enzyme assay are equally applicable to the procedure of the present invention. As should be apparent, in accordance with the present invention, the assay differs from an enzyme assay of the type generally employed in the art by use of a sac of the type hereinabove described (polar group hydrolyzable by an enzyme), including a detectable marker, as the substrate for the enzyme.

The enzyme employed as a label for the tracer is one which hydrolyzes the polar group of the compound employed in producing the sac, i.e., the enzyme changes the polarity of the terminal group. A particularly preferred type of enzyme is a hydrolase such as alkaline phosphatase or sulfatase.

In accordance with a further aspect of the present invention, there is provided a reagent kit or package for accomplishing an assay for an analyte which includes: (a) a tracer comprised of a ligand coupled to an enzyme wherein the ligand is a binder for the analyte (for example an antibody) or the analyte to be assayed or appropriate analog thereof; and (b) sacs which include in the interior thereof a detectable marker wherein at least a portion of the wall of the sac is formed from a compound having structural formula I as hereinabove described. The reagent kit or package may also include an appropriate binder, in supported or unsupported form, with such binder being a binder for at least the analyte, and in some cases, the binder is a binder for both the tracer and the analyte. As known in the art, such binder may be either an antibody or an appropriate naturally recurring binder. The components of the kit may be included in the kit or package in separate containers; for example, vials; however, in some cases, one or more of the components may be combined into a single vial. The kit may also include other components such as standards of the analyte (analyte samples having known concentrations of the analyte), known buffers, and the like. Such kit or package may be employed in an assay for an analyte by use of procedures of the type hereinabove described.

The assay and reagent kit of the present invention may be employed for determining a wide variety of analytes, and has particular applicability to those analytes which are generally found in low concentrations in the material to be assayed. As representative examples of such analytes, there may be mentioned: cardiac glycosides, such as digoxin and digitoxin. Antiasthmatics, such as theophyllin. Antibiotics, such as gentamicin and tobramycin, atineopalastics such as amethotrexate. Anticonvulsants, such as pheno-barbitol, carbamezapine and valparic acid. Antiarrythmics, such as lidocoaine and quinidine. Hormones, such as T4, T3, hCG, TSH, and various steroids. These and other analytes should be apparent to those skilled in the art, and no further teachings in this respect are deemed necessary for a full understanding of the invention. It is to be understood that the scope of the present invention is not to be limited to the representative analytes.

As should be apparent, by employing a sac as hereinabove described, in an enzyme assay, it is possible to produce a sac having a detectable marker, which is not conjugated to a ligand. As a result, the sac has increased stability. Moreover, it is not necessary to produce sacs conjugated to different ligands in order to use the sacs in a wide variety of assays. Moreover, by employing a sac containing a detectable marker, there is an amplification of the signal in that a single tracer molecule is capable of releasing a high concentration of detectable marker.

Although the sacs produced in accordance with the present invention are preferably produced in a manner such that the sacs include a detectable marker; in particular, for use in an enzyme assay, it is to be understood that other materials, such as biologically active materials (therapeutic agents) may be included within the sac. The sacs of the present invention wherein the sacs can be ruptured by an enzyme are not limited to use in an enzyme assay.

The present invention will be further described with respect to the following examples; however, the scope of the invention is not to be limited thereby:

EXAMPLES

Preparation of B-Alanyl-Glycyl-Glycyl-Dioctadecylamide:

N-t-BOC-B-alanyl-glycyl-glycine is prepared by a standard method from N-T-BOC-B-alanine and glycyl-glycine methyl ester, using the DCC and N-hydroxysuccinimide condensation reaction. The ester is hydrolyzed in dilute base and the peptide is recovered by extraction of the acidified (pH 2) reaction mixture.

Add DCC (4.0 g) to a solution of the above peptide (5.3 g) and N-hydroxysuccinimide (2.0 g) in dry THF. After 90 minutes at room temperature, filter, evaporate the filtrate and re-dissolve the residue in dry THF. Add this solution to a suspension of dioctadecylamine (purified by recrystallization from Hexane) (11.0 g) in methylene chloride. After stirring for eighteen (18) hours, the product is isolated by evaporating the reaction mixture to dryness, extracting with hot hexane and chromatographying this extract on silica-gel, using methylene chloride for elution of the pure product. The t-BOC protecting group is removed by dry HCl in dry dioxane.

EXAMPLE 2

Preparation of Hydroxyphenyl Propionate Derivative

Dissolve the peptide from ex. 1 (1.0 g) in ethylacetate containing 100% triethylamine. Add N-succinimidyl-3-(4-hydroxyphenyl)-propionate (1.0 g) (available from Pierce Chemical Company, Rockford, IL). Let react for 24 hours and isolate by chromatography on silica-gel, using methylenechloride:methanol 4:1 mixture.

EXAMPLE 3

Phosphorylation

Dissolve the compound from ex. 2 (0.5 m mole) in triethylphosphate (5 ml) and cool to 0° C. Add phosphoryl chloride (0.5 ml). Keep at 0° C. for 3 hours. Evaporate to dryness. Add water, and after 15 minutes, add triethylamine (3 ml). Evaporate to dryness and purify by chromatography on silica gel, using chloroform:methanol:acetic acid 85:10:5 mixture to elute the pure product.

EXAMPLE 4

Preparation of Dye-Loaded Sacs

Dissolve an equimolar mixture of the material from ex. 3 and cholesterol in a 9:1 mixture of chloroform and methanol. Evaporate to dryness. Add a solution of sulforhodamine B in water (0.1M) at 60° C. sonicate briefly, and wash several times with a buffer solution of the same osmolarity as the encapsulated dye (310 mosm/kg) to prevent osmotic lysis. The vesicles are filtered through 0.4 u filter. The dye-loaded vesicles thus obtained may be used as a highly sensitive substrate in any enzyme immunoassay based on an alkaline-phosphatase as the marker, i.e., alkaline phosphatase linked to an appropriate ligand. Such assay kits are commercially available, and can be used as directed by substituting the kits's substrate with the loaded sacs. The released marker may be quantitated by following the increase in its fluorescence, or by measuring absorption by use of a simple spectrophotometer.

The present invention is advantageous in that the sacs may be employed as a substrate in an enzyme assay; i.e., an assay in which the tracer is formed of ligand coupled to an enzyme. The sacs may be lysed by an enzyme such as an alkaline phosphatase which is often used in an enzyme assay. Sacs which are generally produced from phospholipids are not lysed by alkaline phosphatase and, accordingly, such sacs may not be used as a substrate in an enzyme assay.

Numerous modifications and variations of the present invention are possible in light of the above teachings and, therefore, within the scope of the appended claims, the invention may be practiced otherwise than as particularly described.

What is claimed is:

1. In an assay for an analyte wherein a sample possibly containing analyte is contacted with a tracer having a hydrolase enzyme label to produce a bound tracer fraction and free tracer fraction, and wherein the tracer in at least one of the free and bound tracer fractions is determined as a measure of analyte in the sample, the improvement comprising:

contacting at least one of the free and bound tracer fraction with a sac, said sac including a detactable marker, at least a portion of said sac being formed from a compound having the following structural formula:

X—Y—Z wherein
  X is a hydrophobic radical;

Y is a hydrophilic radical having a polarity which is insufficient to form a vesicle, and is selected from the group consisting of peptide radicals and peptide radicals having a terminal amino acid linked to a hydrocarbon spacer radical having no more than 10 carbon atoms through a peptide like wherein the peptide radical is formed from amino acids having no more than 4 carbon atoms; and Z is a polar group which is hydrolyzable by a hydrolase enzyme.

2. The assay of claim 1 wherein Z is selected from the group consisting of $-PO_4X_1$ and $-SO_4X_1$ wherein $X_1$ is selected from the group consisting of hydrogen and a cation.

3. The assay of claim 2 wherein said compound is

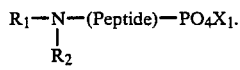

$$R_1-N-(\text{Peptide})-PO_4X_1.$$
$$\phantom{R_1-}|\phantom{-(\text{Peptide})-PO_4X_1.}$$
$$\phantom{R_1-}R_2$$

4. The assay of claim 2 wherein said compound is

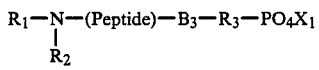

$$R_1-N-(\text{Peptide})-B_3-R_3-PO_4X_1$$
$$\phantom{R_1-}|$$
$$\phantom{R_1-}R_2$$

wherein $B_3$ is selected from the group consisting of $-C(O)-$ and $-NH-$ and forms a peptide linkage with a terminal amino acid of the peptide and $R_3$ is a hydrocarbon radical having no more than 10 carbon atoms.

5. The assay of claim 1 wherein the detectable marker is a chromogen.

6. In an assay for an analyte wherein a sample possibly containing analyte is contacted with a tracer having a hydrolase enzyme label to produce a bound tracer fraction and a free tracer fraction, and wherein the tracer in at least one of the free and bound tracer fractions is determined as a measure of analyte in the sample, the improvement comprising:

contacting at least one of the free and bound tracer fraction with a sac, said sac including a detectable marker, at least a portion of said sac being formed from a compound having the following structural formula:

X—Y—Z wherein

X is a hydrophobic radical selected from the group consisting of radicals having structural formulas II and III

$$R_1-B_1-A-T- \qquad \text{II}$$
$$\phantom{R_1-}|$$
$$\phantom{R_1-}B_2$$
$$\phantom{R_1-}|$$
$$\phantom{R_1-}R_2$$

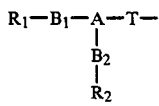

$$R_1-N- \qquad \text{III}$$
$$\phantom{R_1-}|$$
$$\phantom{R_1-}R_2$$

wherein each of $R_1$ and $R_2$ is selected from the groups consisting of substituted and unsubstituted hydrocarbon radicals having at least 11 carbon atoms, each of $B_1$ and $B_2$ is selected from the group consisting of $-CH_2-$; $-C(O)NH-$; NH; $-C(O)O-$; $-O-$; and $-S-$; and T is selected from the groups consisting of $-NH-$, $-R_4F-$, wherein $R_4$ is a hydrocarbon radical having from 1 to 3 carbon atoms and F is selected from the group consisting of $-S-$, $-NH-$, and $-C(O)-$, and A is a hydrocarbon radical having from 1 to 4 carbon atoms Y is a hydrophilic radical having a polarity which is insufficient to form a vesicle; and Z is a polar group which is hydrolyzable by a hydrolase enzyme.

7. The assay of claim 6 wherein Y is selected from the group consisting of peptide radicals and peptide radicals having a terminal amino acid linked to a hydrocarbon spacer radical having no more than 10 carbon atoms through a peptide linkage wherein the peptide radical is formed from amino acids having no more than 4 carbon atoms.

8. The assay of claim 7 wherein Z is selected from the group consisting of $-PO_4X_1$ and $-SO_4X_1$ wherein $X_1$ is selected from the group consisting of hydrogen and a cation.

9. The assay of claim 8 wherein said compound is

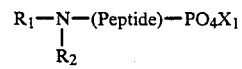

$$R_1-N-(\text{Peptide})-PO_4X_1$$
$$\phantom{R_1-}|$$
$$\phantom{R_1-}R_2$$

10. The assay of claim 8 wherein said compound is

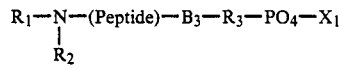

$$R_1-N-(\text{Peptide})-B_3-R_3-PO_4-X_1$$
$$\phantom{R_1-}|$$
$$\phantom{R_1-}R_2$$

wherein $B_3$ is selected from the group consisting of $-C(O)-$ and $-NH-$ and forms a peptide linkage with a terminal amino acid of the peptide and $R_3$ is a hydrocarbon radical having no more than 10 carbon atoms.

11. The assay of claim 6 wherein the enzyme label is alkaline phosphatase.

12. The assay of claim 6 wherein the detectable marker is a chromogen.

13. In an assay for an analyte wherein a sample possibly containing analyte is contacted with a tracer having an alkaline phosphatase label to produce a bound tracer fraction and a free tracer fraction, and wherein the tracer in at least one of the free and bound tracer fractions is determined as a measure of analyte in the sample, the improvement comprising:

contacting at least one of the free and bound tracer fraction with a sac, said sac including a detectable marker, at least a portion of said sac being formed from a compound having the following structural formula:

X—Y—Z wherein

X is a hydrophobic radical;

Y is a hydrophilic radical having a polarity which is insufficient to form a vesicle; and

Z is a polar group which is hydrolyzable by said alkaline phosphatase.

14. The assay of claim 13 wherein Y is selected from the group consisting of peptide radicals and peptide radicals having a terminal amino acid linked to a hydrocarbon spacer radical having no more than 10 carbon atoms through a peptide linkage wherein the peptide radical is formed from amino acids having no more than 4 carbon atoms.

15. The assay of claim 14 wherein Z is —PO$_4$X$_1$ and wherein X$_1$ is selected from the group consisting of hydrogen and a cation.

16. The assay of claim 15 wherein said compound is $$R_1-N(R_2)-(Peptide)-PO_4X_1$$

17. The assay of claim 15 wherein said compound is $$R_1-N(R_2)-(Peptide)-B_3-R_3-PO_4X_1$$

wherein B$_3$ is selected from the group consisting of —C(O)— and —NH— and forms a peptide linkage with a terminal amino acid of the peptide and R$_3$ is a hydrocarbon radical having no more than 10 carbon atoms.

18. The assay of claim 13 wherein the detectable marker is a chromogen.

19. A reagent kit for determining an analyte, comprising:
a package, said package containing a sac and a tracer having an alkaline phosphatase label, said sac including a detectable marker and being lysable by said alkaline phosphatase label, at least a portion of said sac being formed from a compound having the following structural formula:

$$X-Y-Z$$

wherein
X is a hydrophobic radical;
Y is a hydrophilic radical having a polarity which is insufficient to form a vesicle; and
Z is a polar group which is hydrolyzable by said alkaline phosphatase.

20. The reagent kit of claim 19 wherein the detactable marker is a chromogen.

21. The reagent kit of claim 19 wherein Z is —PO$_4$X$_1$ and wherein X$_1$ is selected from the group consisting of hydrogen and a cation.

22. The reagent kit of claim 21 wherein said compound is $$R_1-N(R_2)-(Peptide)-PO_4X_1.$$

23. The reagent kit of claim 21 wherein said compound is $$R_1-N(R_2)-(Peptide)-B_3-R_3-PO_4X_1$$

wherein B$_3$ is selected from the group consisting of —C(O)— and —NH— and forms a peptide linkage with a terminal amino acid of the peptide and R$_3$ is a hydrocarbon radical having no more than 10 carbon atoms.

24. A reagent kit for determining an analyte comprising:
a package, said package containing a sac and a tracer having an hydrolase enzyme label, said sac including a detactable marker, and being lysable by said hydrolase enzyme alkaline phosphatase label, at least a portion of said sac being formed from a compound having the following structural formula:

$$X-Y-Z$$

wherein
X is a hydrophobic radical selected from the group consisting of radicals having structural formulas II and III $$R_1-B_1-A(B_2)(R_2)-T-$$

wherein each of R$_1$ and R$_2$ is selected from the groups consisting of substituted and unsubstituted hydrocarbon radicals having at least 11 carbon atoms, each of B$_1$ and B$_2$ is selected from the group consisting of —CH$_2$—; —C(O)NH—; —NH—; —C(O)O—; —O—; —S—
T is selected from the group consisting of —NH—, —R$_4$—F— wherein R$_4$ is a hydrocarbon radical having from 1 to 3 carbon atoms and F is selected from the group consisting of —S—, —NH—, and —C(O)—, and A is a hydrocarbon radical having from 1 to 4 carbon atoms;
Y is a hydrophilic radical having a polarity which is insufficient to form a vesicle; and
Z is polar group which is hydrolyzable by said hydrolase enzyme.

25. The reagent kit of claim 24 wherein Y is selected from the group consisting of peptide radicals and peptide radicals having a terminal amino acid linked to a hydrocarbon spacer radical having no more than 10 carbon atoms through a peptide linkage wherein the peptide radical is formed from amino acids having no more than 4 carbon atoms.

26. The reagent kit of claim 25 wherein Z is selected from the group consisting of —PO$_4$X$_1$ and —SO$_4$X$_1$ wherein X$_1$ is selected from the group consisting of hydrogen and a cation.

27. The reagent kit of claim 26 wherein said compound is $$R_1-N(R_2)-(Peptide)-PO_4X_1.$$

28. The reagent kit of claim 26 wherein said compound is $$R_1-N(R_2)-(Peptide)-B_3R_3-PO_4X_1$$

wherein B$_3$ is selected from the group consisting of —C(O)— and —NH— and forms a peptide linkage with a terminal amino acid of the peptide and R$_3$ is a hydrocarbon radical having no more than 10 carbon atoms.

29. The reagent kit of claim 24 wherein the detectable marker is a chromogen.

30. A reagent kit for determining analyte, comprising:
a package, said package containing a sac and a tracer having an hydrolase enzyme label, said sac including a detectable marker, and being lysable by said hydrolase enzyme label, at least a portion of said sac being formed from a compound having the following structural formula:

X—Y—Z, wherein

X is a hydrophobic radical;

Y is a hydrophilic radical having a polarity which is insufficient to form a vesicle, with Y being selected from the group consisting of peptide radicals and peptide radicals having a terminal amino acid linked to a hydrocarbon spacer radical having no more than 10 carbon atoms through a peptide linkage wherein the peptide radical is formed from amino acids having no more than 4 carbon atoms; and Z is a polar group which is hydrolyzable by said hydrolase enzyme.

31. The reagent kit of claim 30 wherein Z is selected from the group consisting of —PO$_4$X$_1$ and —SO$_4$X$_1$ wherein X$_1$ is selected from the group consisting of hydrogen and a cation.

32. The reagent kit of claim 31 wherein said compound is

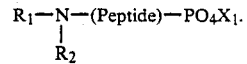

33. The reagent kit of claim 31 wherein said compound is

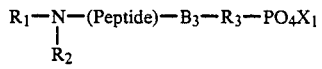

wherein B$_3$ is selected from the group consisting of —C(O)— and —NH— and forms a peptide linkage with a terminal amino acid of the peptide and R$_3$ is a hydrocarbon radical having no more than 10 carbon atoms.

34. The reagent kit of claim 30 wherein the detectable marker is a chromogen.

* * * * *